United States Patent
Laroche et al.

(10) Patent No.: US 10,414,702 B2
(45) Date of Patent: Sep. 17, 2019

(54) METHOD FOR SEPARATING XYLENES IN A SIMULATED MOVING BED BY MEANS OF A ZEOLITIC ADSORBENT SOLID HAVING A PARTICLE SIZE OF BETWEEN 150 AND 500 MICRONS

(71) Applicants: IFP ENERGIES NOUVELLES, Rueil-malmaison (FR); Arkema France, Colombes (FR)

(72) Inventors: Catherine Laroche, Vernaison (FR); Damien Leinekugel Le Cocq, Lyons (FR); Philibert LeFlaive, Mions (FR); Frederic Augier, Saint Symphorien D'Ozon (FR); Ludivine Bouvier, Orthez (FR); Cecile Lutz, Gan (FR); Sylvie Szendrovics, Arthez-de-Bearn (FR); Quitterie Persillon, Morlaas (FR)

(73) Assignees: IFP ENERGIES NOUVELLES, Reuil-malmaison (FR); Arkema France, Colombes (FR)

( * ) Notice: Subject to any disclaimer, the term of this patent is extended or adjusted under 35 U.S.C. 154(b) by 215 days.

(21) Appl. No.: 14/769,702

(22) PCT Filed: Feb. 18, 2014

(86) PCT No.: PCT/EP2014/053138
§ 371 (c)(1),
(2) Date: Aug. 21, 2015

(87) PCT Pub. No.: WO2014/128125
PCT Pub. Date: Aug. 28, 2014

(65) Prior Publication Data
US 2016/0009614 A1    Jan. 14, 2016

(30) Foreign Application Priority Data
Feb. 22, 2013  (FR) .................................... 1351536

(51) Int. Cl.
*C07C 7/12*  (2006.01)
*C07C 7/13*  (2006.01)
(Continued)

(52) U.S. Cl.
CPC ............ *C07C 7/13* (2013.01); *B01D 15/1828* (2013.01); *B01J 20/183* (2013.01); *B01J 20/186* (2013.01);
(Continued)

(58) Field of Classification Search
CPC .................................... C07C 7/12; C07C 7/13
(Continued)

(56) References Cited

U.S. PATENT DOCUMENTS 3,558,730 A  1/1971  Neuzil
3,663,638 A  5/1972  Neuzil
(Continued)

FOREIGN PATENT DOCUMENTS

FR    2693186    1/1994
FR    2795407    12/2000
(Continued)

OTHER PUBLICATIONS

International Search Report for International Application No. PCT/EP2014/053138 dated Apr. 1, 2014.
(Continued)

*Primary Examiner* — Thuan D Dang
(74) *Attorney, Agent, or Firm* — RatnerPrestia

(57) ABSTRACT

Process for separating xylenes starting from a feed comprising cuts of isomers of aromatic hydrocarbons containing 8 carbon atoms, in a simulated moving bed, by selective adsorption of a xylene isomer in the presence of a desorbent, by means of particles of agglomerated zeolitic adsorbent based on zeolite crystals with a number-average diameter less than or equal to 1.2 μm, wherein the number-average (Continued)

Figure 1:
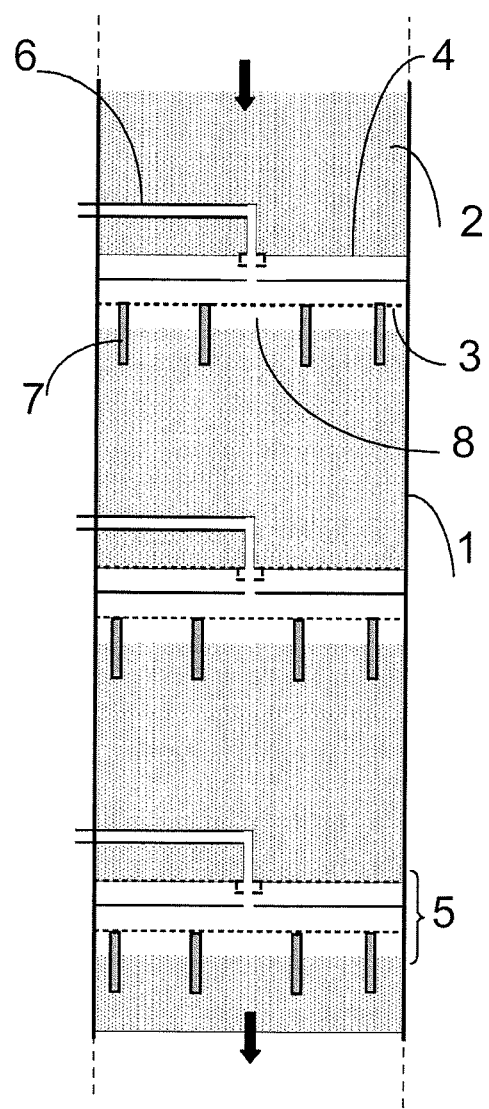

diameter of said particles of adsorbent is between 150 μm and 500 μm and the mechanical strength measured by the Shell method series SMS1471-74 adapted for agglomerates with a size below 500 μm is greater than or equal to 2 MPa.

20 Claims, 3 Drawing Sheets

(51) Int. Cl.
*B01D 15/18* (2006.01)
*B01J 20/18* (2006.01)
*B01J 20/28* (2006.01)

(52) U.S. Cl.
CPC ... *B01J 20/28004* (2013.01); *B01J 20/28011* (2013.01); *B01J 20/28019* (2013.01); *B01J 20/28052* (2013.01); *B01J 20/28071* (2013.01)

(58) Field of Classification Search
USPC .................................................. 585/825, 828
See application file for complete search history.

(56) References Cited

U.S. PATENT DOCUMENTS

| | | | |
|---|---|---|---|
| 3,761,533 A | 9/1973 | Otani et al. | |
| 3,960,774 A | 6/1976 | Rosback | |
| 5,107,062 A | 4/1992 | Zinnen | |
| 5,382,747 A | 1/1995 | Kulprathipanja | |
| 5,401,476 A | 3/1995 | Hotier et al. | |
| 5,716,593 A | 2/1998 | Miller | |
| 5,948,950 A | 9/1999 | Hotier et al. | |
| 6,136,198 A | 10/2000 | Adam | |
| 6,376,734 B1 | 4/2002 | Magne-Drisch | |
| 6,410,815 B1 | 6/2002 | Plee | |
| 6,706,938 B2 | 3/2004 | Roeseler | |
| 6,884,918 B1 | 4/2005 | Plee | |
| 7,208,651 B2 | 4/2007 | Frey | |
| 7,728,187 B2 | 6/2010 | Kulprathipanja | |
| 7,812,208 B2 | 10/2010 | Cheng | |
| 7,820,869 B2 | 10/2010 | Priegnitz | |
| 8,530,367 B2 | 9/2013 | Bouvier | |
| 8,735,643 B2 | 5/2014 | Bouvier | |
| 9,079,163 B2 | 7/2015 | Nakaoka et al. | |
| 2002/0107427 A1 | 8/2002 | Doyle et al. | |
| 2007/0038012 A1 | 2/2007 | Leflaive et al. | |
| 2007/0043253 A1 | 2/2007 | Leflaive et al. | |
| 2009/0326308 A1* | 12/2009 | Kulprathipanja | B01J 20/183 585/820 |
| 2009/0326309 A1 | 12/2009 | Priegnitz | |
| 2009/0326310 A1* | 12/2009 | Kulprathipanja | B01J 20/183 585/828 |
| 2010/0113854 A1 | 5/2010 | Bouvier et al. | |
| 2011/0105301 A1* | 5/2011 | Wang | B01J 20/183 502/62 |
| 2011/0184165 A1 | 7/2011 | Bouvier et al. | |

FOREIGN PATENT DOCUMENTS

| | | |
|---|---|---|
| FR | 2903978 | 1/2008 |
| FR | 2925366 | 6/2009 |
| JP | 5010547 B1 | 4/1975 |
| JP | 05201886 A | 8/1993 |
| JP | 08217700 A | 8/1996 |
| JP | 2001507007 A | 5/2001 |
| JP | 2001525781 A | 12/2001 |
| JP | 2009543688 A | 12/2009 |
| WO | 2008009845 | 1/2008 |
| WO | 2009081023 | 7/2009 |
| WO | 2011118668 A1 | 9/2011 |

OTHER PUBLICATIONS

Gomes, P. et al., "Simulated moving bed technology: old and new," 2006, pp. 375-392, vol. 12, Adsorption (abstract only).
Notification of Reasons for Refusal for Japanese Application No. 2015-558424, dated Aug. 23, 2016 with translation, 8 pages.

* cited by examiner

METHOD FOR SEPARATING XYLENES IN A SIMULATED MOVING BED BY MEANS OF A ZEOLITIC ADSORBENT SOLID HAVING A PARTICLE SIZE OF BETWEEN 150 AND 500 MICRONS

CROSS-REFERENCE TO RELATED APPLICATIONS

This application is a national phase of International Application No. PCT/EP2014/053138, filed Feb. 18, 2014, which claims priority from French Application No. 1351536, filed Feb. 22, 2013. The entire disclosures of each of these applications are incorporated herein by reference in their entirety for all purposes.

FIELD OF THE INVENTION

The present invention relates to the area of processes for simulated moving-bed (SMB) separation of xylenes.

The aim of the invention is to improve the long-term productivity of existing processes by acting on the granulometry characteristics of the particles of adsorbent solid.

Simulated moving-bed separation is to be understood here in the broad sense, i.e. we may be dealing with simulated counter-current, or with simulated co-current, or with a so-called "varicol" process.

A characteristic feature common to this family of processes is that the adsorbent solid is employed in a fixed bed, and that the liquid streams in contact with the adsorbent are managed either by means of a set of all-or-nothing valves, or by means of a complex single valve known as a rotary valve.

When the active element of the adsorbent solids used as adsorption agents in these processes is a zeolite, the latter, obtained in the form of powder, is preferably used on an industrial scale in the form of agglomerates. These zeolitic adsorbents, agglomerated in the form of platelets, beads or extrudates, generally consist of a zeolite powder, which constitutes the active element in the sense of adsorption, and of a binder intended to ensure cohesion of the crystals in the form of grains. This binder also endows the grains with sufficient mechanical strength to withstand the mechanical stresses to which they are subjected while they are in use in the units. These mechanical stresses are the cause of the formation of fines, which lead to a deterioration of performance with increasing process time.

The process for simulated moving-bed (SMB) separation of xylenes has undergone numerous technological improvements, notably at the level of the fluid distributing plates, but there has been relatively little progress regarding the granulometric characteristics of the particles of the adsorbent solid.

TECHNOLOGICAL BACKGROUND

The following properties are required for the zeolitic adsorbent solid:

Maximum possible adsorption capacity of the zeolitic agglomerate, i.e. highest possible zeolite content, since the zeolite constitutes the microporosity within which the adsorption takes place.

Maximum possible transfer within the zeolitic agglomerate, i.e. minimum time for passage of a hydrocarbon molecule from the exterior of the agglomerate to the centre of the zeolite crystals of the zeolitic adsorbent.

Highest possible crushing strength of the zeolitic agglomerate, and in all cases above 1.7 MPa as measured by the Shell test of fixed-bed crushing strength, modified to adapt to the granulometry of the agglomerates.

Documents of the prior art describing the chemical and microscopic characteristics of the zeolitic adsorbents used for separating para-xylene are particularly numerous, for example (U.S. Pat. Nos. 3,558,730; 3,663,638 (Neuzil); U.S. Pat. No. 3,960,774 (Rosback); U.S. Pat. No. 6,706,938 (Roeseler); U.S. Pat. No. 7,820,869 (Priegnitz); U.S. Pat. No. 7,812,208 (Cheng); U.S. Pat. Nos. 6,410,815; 6,884,918 (Plee); WO08/009845; WO09/081023 (Bouvier); US2011/105301 (Wang)).

The general teaching concerning the chemical characteristics of these adsorbent solids is that it is necessary to use a zeolite of faujasite structure (zeolite LSX, X or Y) exchanged with barium (to at least 90%, expressed in degree of exchange) or exchanged very predominantly with barium and to a minor extent with potassium (for example from 2 to 33%). For separating meta-xylene, U.S. Pat. No. 5,382,747 (Kulprathipanja) teaches the use of a sodium zeolite Y or of a sodium zeolite Y partially exchanged with lithium.

The general teaching concerning the microscopic characteristics of the adsorbent is that it is possible to use crystals of zeolite LSX with a size preferably below 2 microns (number-average diameter) or crystals of zeolite X with a size preferably below 1.6 microns (number-average diameter). The size of the crystals of conventional zeolite Y is of the order of 1 to 3 µm, and U.S. Pat. No. 7,728,187 (Kulprathipanja) recommends using nanocrystals of zeolite Y, with size between 50 and 700 nm, to improve the mass transfer of the meta-xylene.

An additional characteristic of these zeolites is that they must be hydrated so as to have an acceptable microporous transfer (U.S. Pat. No. 5,107,062 (Zinnen)).

Obtaining a microporous transfer that is as high as possible is, however, inconsistent with obtaining a maximum possible adsorption capacity, since the presence of water in the zeolitic structure will reduce the total capacity for adsorption of the xylenes as well as the capacity for selective adsorption of para-xylene (U.S. Pat. No. 7,820,869 (Priegnitz) or meta-xylene (U.S. Pat. No. 5,382,747 (Kulprathipanja)).

Consequently, it is sometimes necessary to adjust the hydration of the zeolite to achieve a compromise between acceptable microporous transfer and acceptable selective adsorption capacity. The degree of hydration of the adsorbent can be adjusted by varying the conditions of final activation of the adsorbent (i.e. temperature, duration etc.), which constitutes the last step in manufacture of the adsorbent.

The extent of hydration of the adsorbent can be evaluated approximately by measuring the loss on ignition, which can be carried out on the adsorbent before it is fed into the unit and brought in contact with the xylenes. Typically a zeolite LSX or a zeolite X must have a loss on ignition at 900° C. between 4 and 7.7% and a zeolite Y must have a loss on ignition at 900° C. between 0 and 3%.

The general teaching concerning the macroscopic characteristics of the adsorbent is that the content of active material can be increased by converting the binder to zeolite under the action of a basic alkaline solution, so that the finished product contains a reduced amount of non-zeolitic phase, which can be quantified by reference to an adsorbent composed solely of zeolite, in the form of powder, on the basis of measurements of adsorption or on the basis of intensities of XRD peaks. Moreover, this conversion of the binder to active material in the sense of adsorption allows the mechanical strength of the agglomerate to be maintained (WO08/009845 (Bouvier)), which is necessary for withstanding the mechanical stresses during its application in the units.

Another general teaching concerning the macroscopic characteristics of the adsorbent is that the agglomerates are generally of granulometry between 0.2 mm and 1.5 mm and more particularly between 0.25 and 1.2 mm (16-60 Standard US Mesh size—U.S. Pat. No. 7,820,869 (Priegnitz)) or between 0.35 and 0.8 mm (Example 1 US2011/105301 (Wang)). This granulometric range is obtained by sieving and/or cycloning at the end of the agglomerate forming step. The documents cited above provide indications for the "size range", i.e. the granulometric range of the agglomerates, and not for the average diameter of these agglomerates. WO08/009845 and WO09/081023 (Bouvier) teach that the agglomerates generally have a number-average diameter ranging from 0.4 to 2 mm and in particular from 0.4 to 0.8 mm.

In the process for separating xylenes by simulated moving-bed adsorption, the zeolitic adsorbent solid is brought in contact with the liquid feed stream (the feed) composed of the mixture of xylenes, containing ortho-xylene, meta-xylene, para-xylene and ethylbenzene.

By using a zeolitic adsorbent based on zeolite of faujasite structure with an Si/Al ratio between 1 and 1.5 (zeolite LSX, X) exchanged with barium (to at least 90% expressed in degree of exchange) or exchanged very predominantly with barium and to a minor extent with potassium, the para-xylene is then adsorbed in the micropores of the zeolite preferentially relative to all of the other hydrocarbon compounds present in the feed stream. The phase adsorbed in the micropores of the zeolite is then enriched with para-xylene relative to the initial mixture constituting the feed stream. In contrast, the liquid phase is enriched with compounds such as ortho-xylene, meta-xylene and ethylbenzene in higher relative proportion than that characterizing the initial mixture constituting the feed stream.

By using a zeolitic adsorbent based on zeolite of faujasite structure with an Si/Al ratio in the range $1.5<Si/Al<6$ (zeolite Y) exchanged with sodium or exchanged with sodium and lithium, the meta-xylene is then adsorbed in the micropores of the zeolite preferentially relative to all of the other hydrocarbon compounds present in the feed stream. The phase adsorbed in the micropores of the zeolite is then enriched with meta-xylene relative to the initial mixture constituting the feed stream. In contrast, the liquid phase is enriched with compounds such as ortho-xylene, para-xylene and ethylbenzene in higher relative proportion than that characterizing the initial mixture constituting the feed stream.

The liquid phase is withdrawn from contact with the adsorbent, thus forming a raffinate stream.

The adsorbed phase, enriched with para-xylene or meta-xylene depending on the zeolite used in the adsorbent, is desorbed under the action of a stream of desorbent, and withdrawn from contact with the adsorbent, then forming a stream of extract.

Maintaining the hydration of the zeolite at the desired value, for example a loss on ignition from 4% to 7.7% for zeolite X or LSX and 0 to 3% for zeolite Y, while it is used in the process for separating xylenes by simulated moving-bed adsorption, is assured by adding water to the incoming streams of the feed and/or of desorbent. The addition of water necessary for these levels of loss on ignition is such that the water content by weight in the hydrocarbon effluents (the stream of extract or of raffinate) is between 0 ppm and 150 ppm (40-150 ppm when the adsorbent is based on zeolite X or LSX and 0-80 ppm when the adsorbent is based on zeolite Y).

In the process for separating xylenes by simulated moving-bed adsorption, the zeolitic adsorbent solid is employed in one or two multistage columns for bringing in contact with the liquid stream. Multistage column is the name used for a column consisting of a multiplicity of plates arranged along an approximately vertical axis, each plate supporting a bed of granular solid, with the different successive beds being traversed in series by the fluid or fluids employed in the column. A device for distributing the fluids is arranged between two successive beds, providing feed to each bed of granular solid.

The bed of granular solid can be blocked by the distributing device, but most often there is an empty space between the distributing device and the surface of the bed of granular solid downstream in order to allow a slight sagging of the distributing device.

In general, the operation of a simulated moving-bed column can be described as follows:

A column comprises at least four zones, and optionally five or six, each of these zones consisting of a certain number of successive beds, and each zone being defined by its position between a feed point and a withdrawal point. Typically, an SCC unit for producing para-xylene or for producing meta-xylene is supplied with at least one feed F to be fractionated (feed of aromatic hydrocarbons consisting of isomers with 8 carbon atoms) and a desorbent D, sometimes called eluent (generally paradiethyl benzene or toluene), and at least one raffinate R is withdrawn from said unit, containing the products of the feed the least selectively adsorbed and the desorbent and an extract E containing the feed product adsorbed the most and the desorbent.

Other points for injection and withdrawal can be added so as to rinse the distributing circuits, as described for example in U.S. Pat. No. 7,208,651. Adding these additional rinsing streams does not in any way change the operating principle of the SCC, and for the sake of brevity, we shall not add these additional points for injection and withdrawal in the description of the process according to the invention.

The points for feed and withdrawal are modified over time, displaced in the same direction from a value corresponding to one bed. The shifts of the different points of injection or of withdrawal can be either simultaneous, or non-simultaneous as taught in U.S. Pat. No. 6,136,198. The process according to this second operating mode is called VARICOL.

Conventionally, 4 different chromatographic zones are defined in a column operating in simulated counter-current (SCC).

Zone 1: zone of desorption of the feed product adsorbed the most, comprised between injection of the desorbent D and withdrawal of the extract E.

Zone 2: zone of desorption of the feed products the least selectively adsorbed, comprised between withdrawal of the extract E and injection of the feed to be fractionated F.

Zone 3: zone of adsorption of the feed product adsorbed the most, comprised between injection of the feed and withdrawal of the raffinate R.

Zone 4: zone situated between withdrawal of the raffinate R and injection of the desorbent D.

To increase the productivity of the separation process, we shall try to obtain zeolitic adsorbents of the smallest possible diameter in order to increase the transfer.

The documents of the prior art describing processes for pharmaceutical separation (Gomes et al., 2006, Adsorption, Vol. 12, p. 375) report processes for chromatographic separation in the liquid phase using agglomerates from some tens of micrometers to 100 μm.

In these processes using agglomerates of very small size, the head loss ΔP is then high. In the processes for separating xylenes, such levels of head loss ΔP are uncommon. Nevertheless, it is noted that, surprisingly, the head loss ΔP is not a determining criterion. It will have an effect notably on the thickness of the walls of the adsorber and on the output of the installations.

In the process for separating xylenes by simulated moving-bed adsorption, the zeolitic adsorbent is supported by plates forming successive beds of granular solid traversed in series by the fluid or fluids employed in the column. A device is positioned between two successive beds for distributing the fluids for providing feed to each bed of granular solid, and most often there is an empty space between the distributing device and the surface of the bed of granular solid downstream.

The plates can be cut in panels of the parallel type (meridian panels) or radial type (pie-cut panels). Each plate is delimited by a lower grid and an upper grid. A space not containing adsorbent is situated between the lower grid of a plate and the top of the bed placed under the plate in question. This space is necessary to avoid any phenomenon of mechanical degradation of the adsorbent solid connected with sagging of the plate.

Inherently in distribution, there is a tangential component of flow which promotes the phenomenon of partial fluidization or of entrainment of the particles at the surface of the bed of granular solid, causing the formation of furrows or banks on the surface of the bed. This phenomenon is promoted by high velocities of circulation and small particle diameters.

The formation of banks has two harmful effects on operation of the unit. On the one hand, it perturbs the flow and generates delays of residence time, degrading the separation performance. On the other hand, it promotes crushing of the sieve by the plates or the plate supports. Now, the service life of the sieve is largely linked to the generation of fines through crushing of the sieve.

It was discovered that by choosing a particular size range of the beads for an agglomerated zeolitic adsorbent, it was possible to overcome such phenomena, and thus increase the service life of the sieve.

The present invention describes a process employing an agglomerated adsorbent whose particular granulometry is selected so as to avoid degradation of the performance of the process in the long term. By choosing the particular granulometry it is possible to avoid the formation of banks on the surface of the beds of granular solid in the column or columns of the simulated moving bed.

The present invention thus proposes a process for separating xylenes using an agglomerated adsorbent of reduced granulometry, preferably based on faujasite zeolite with an Si/Al ratio between 1 and 6, for producing para-xylene or meta-xylene at high purity with a permanently improved productivity, while avoiding degradation of performance over time.

DESCRIPTION OF THE INVENTION

Summary of the Invention

The invention relates to a process for separating xylenes starting from a feed comprising cuts of isomers of aromatic hydrocarbons containing 8 carbon atoms, in a simulated moving bed, by selective adsorption of a xylene isomer in the presence of a desorbent, by means of particles of agglomerated zeolitic adsorbent based on zeolite crystals with a number-average diameter less than or equal to 1.2 μm, in which the number-average diameter of said particles of adsorbent is between 150 μm and 500 μm and the mechanical strength measured by the Shell method series SMS1471-74 adapted for agglomerates with a size below 500 μm is greater than or equal to 2 MPa.

The number-average diameter of said particles of adsorbent is preferably between 200 μm and 400 μm.

Preferably, the granulometric distribution of said particles of adsorbent is such that no particle exists with size less than 100 μm.

Preferably, the number-average diameter of the zeolite crystals is between 0.1 μm and 1.2 μm.

Very preferably, the number-average diameter of the zeolite crystals is between 0.5 μm and 0.8 μm.

Any range of values denoted by the expression "between a and b" represents the domain of values from more than a to less than b (i.e. limits a and b excluded), whereas any range of values denoted by the expression "from a to b" signifies the domain of values ranging from a to b (i.e. including the limits a and b).

The process for separating xylenes can be implemented in a simulated moving-bed unit having the following characteristics:
  number of beds between 4 and 24
  number of zones: at least 4.

Advantageously, the cycle time, corresponding to the time between two injections of desorbent on a given bed, is between 4 and 18 min.

Advantageously, the process for separating xylenes operates at a temperature from 100° C. to 250° C., preferably 120° C. to 190° C. and at a pressure between the bubble pressure of the xylenes at the process temperature and 3 MPa.

Advantageously, the ratio of the flow rates of desorbent to feed is between 0.7 and 2.5 and the recycling rate is between 2.0 and 12, preferably 2.5 to 4.

In one embodiment, the invention also relates to a process for separating para-xylene by selective adsorption of para-xylene in which the agglomerated zeolitic adsorbent is based on zeolite X or LSX having an Si/Al atomic ratio such that 1.0<Si/Al<1.5, preferably such that 1.1<Si/Al<1.5 and even more preferably such that 1.2<Si/Al<1.3.

In this case, the agglomerated zeolitic adsorbent can further comprise:
  A content of barium oxide BaO and a content of potassium oxide $K_2O$ such that the ratio of the number of moles of the total barium oxide+potassium oxide $(BaO+K_2O)$ to the number of moles of the total $(BaO+K_2O+Na_2O)$ is greater than 90%;
  A content of potassium oxide $K_2O$ such that the ratio of the number of moles of potassium oxide $K_2O$ to the number of moles of barium oxide BaO is less than 0.5;
  and a total content of oxides of alkali-metal or alkaline-earth ions other than barium and potassium preferably less than 5% and preferably ranging from 0 to 2 wt % and advantageously ranging from 0 to 1 wt % relative to the total weight of the zeolitic adsorbent.

In this case, the agglomerated zeolitic adsorbent can have a grain density between 1.1 and 1.4 g/mL, and preferably between 1.1 and 1.3 g/mL as measured by mercury intrusion (expressed relative to the dry mass of the zeolitic adsorbent) and a total pore volume measured by mercury intrusion (pore volume contained in the macropores and the mesopores with apparent diameter greater than 4 nm) between 0.20 and 0.35 mL/g (expressed relative to the dry mass of the zeolitic adsorbent).

The process for separating para-xylene can be carried out at a temperature from 165° C. to 185° C. and the water content in the hydrocarbon effluents is adjusted between 20 ppm and 150 ppm, by adding water to the feed comprising the cuts of isomers of aromatic hydrocarbons containing 8 carbon atoms and/or to the desorbent.

In said process for separating para-xylene the desorbent is preferably selected from toluene and para-diethylbenzene.

In another embodiment, the invention relates to a process for separating meta-xylene by selective adsorption of meta-xylene, in which the agglomerated zeolitic adsorbent is based on zeolite Y having an Si/Al atomic ratio such that 1.5<Si/Al<6, preferably such that 2.5<Si/Al<3.

In this case the agglomerated zeolitic adsorbent can further comprise:
- A content of sodium oxide $Na_2O$ and a content of lithium oxide $Li_2O$ such that the ratio of the number of moles of sodium oxide to the number of moles of the total sodium oxide+lithium oxide ($Na_2O+Li_2O$) is greater than 65%.
- and a total content of oxides of alkali-metal or alkaline-earth ions other than sodium and lithium preferably less than 5% and preferably ranging from 0 to 2 wt % and advantageously ranging from 0 to 1 wt % relative to the total weight of the zeolitic adsorbent.

The process for separating meta-xylene can be carried out at a temperature from 120° C. to 180° C. and the water content in the hydrocarbon effluents is adjusted between 0 ppm and 80 ppm, by adding water to the feed comprising the cuts of isomers of aromatic hydrocarbons containing 8 carbon atoms and/or to the desorbent.

In the process for separating meta-xylene according to the invention, the desorbent is preferably selected from toluene and indane.

The invention also relates to a process for separating para-xylene of high purity.

The invention also relates to a process for separating meta-xylene of high purity.

LIST OF FIGURES

Figure 2:
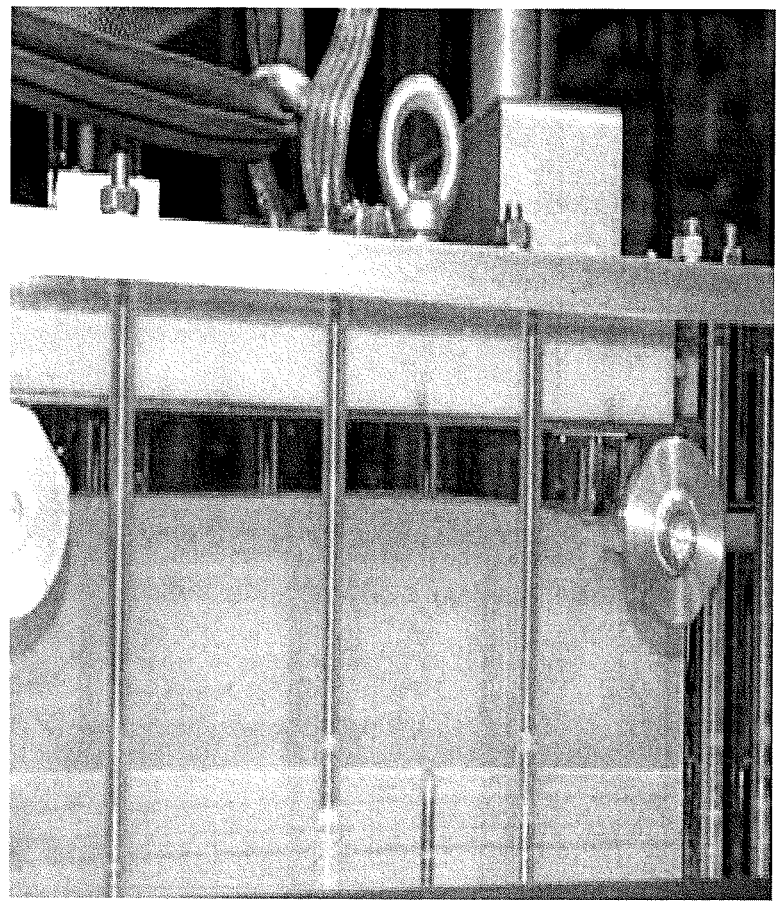
Figure 3:

FIGS. 1 to 3 illustrate the invention and are presented non-exhaustively.

FIG. 1: Schematic diagram of a multistage column with simulated moving-bed operation FIG. 2: Photograph of the results obtained in cold mock-up for the process for separating xylenes using the formulations of adsorbent according to the invention A to D: absence of formation of furrows or banks on the surface of the granular bed at the maximum linear surface velocity of 1.65 cm/s after 4 hours under flow, i.e. absence of deformation on the surface of the granular bed relative to the horizontal line passing by the surface of the bed at the beginning of the test (Example 2).

FIG. 3: Photograph of the results obtained in cold mock-up for the process for separating xylenes using the formulations of adsorbent E and F (comparative tests): formation of furrows or banks on the surface of the granular bed for linear surface velocities below 1.65 cm/s, appearing after the first 20 minutes of the test. On the photograph, taken after 4 hours under flow, a deformation of the surface of the bed is observed in such a way that the heights of the bed at the lowest point and at the highest point of the height profile of the bed at the end of the test differ respectively by 70% and by 40% of the initial height of the granular bed (Example 3).

BRIEF DESCRIPTION OF FIG. 1

The appended FIG. 1 shows a multistage column with distributor plates with simulated moving-bed operation. This figure is provided purely for purposes of illustration.

The column in the enclosure (1) is divided into a certain number of granular beds (2). A distributor plate (5), supported on beams (7), is interposed between two successive granular beds, designated upstream bed and downstream bed. An upper grid (4) supports the granular medium (2) while allowing the fluid to go back into the plate.

The distributing devices also comprise a distribution network (6) immersed in the granular medium (2), for injecting or withdrawing an auxiliary fluid into or from the plate. In the case of injection, the auxiliary fluid injected is thus mixed with the main fluid coming from the upstream bed.

The distributor plate (5) also comprises a lower grid (3) or perforated plate, or any other means for distributing the flow on the downstream granular bed. There is an empty space (8) between the lower grid (3) and the upper surface of the downstream granular bed.

DETAILED DESCRIPTION OF THE INVENTION

The invention relates to a process for separating xylenes starting from C8 cuts of aromatic isomers in a simulated moving bed (SMB) consisting of using, as adsorbent solid selectively retaining a xylene isomer, an agglomerated zeolitic adsorbent having in addition particular characteristics of granulometry at the level of the size of the zeolitic adsorbents. The particles of agglomerated zeolitic adsorbent solid used in the process according to the invention have a (number-) average particle diameter between 150 µm and 500 µm, preferably between 200 µm and 400 µm. Preferably, the particles have a granulometric distribution such that there is no particle with size less than 100 µm.

More particularly, the following will be selected, for selectively adsorbing:
(1) para-xylene, zeolitic adsorbents based on zeolite X or LSX, exchanged with barium (to at least 90% expressed in degree of exchange on the final agglomerate, estimated by evaluating the ratio of the number of moles of barium oxide, BaO, to the number of moles of the total ($BaO+Na_2O$) of the final agglomerate), or exchanged very predominantly with barium, and to a minor extent with potassium (the degree of exchange with barium and potassium ions being at least 90%, estimated by evaluating the ratio of the number of moles of the total barium oxide+potassium oxide ($BaO+K_2O$) to the number of moles of the total ($BaO+K_2O+Na_2O$)) of the final agglomerate,
or (2) meta-xylene, zeolitic adsorbents based on zeolite Y, with sodium or exchanged with sodium and lithium such that the ratio of the number of moles of sodium oxide $Na_2O$ to the number of moles of the total sodium oxide+lithium oxide ($Na_2O+Li_2O$) of the final agglomerate is greater than 65%,
this adsorbent solid moreover having particular characteristics of granulometry at the level of the size of the zeolitic adsorbents.

The process according to the present invention can be carried out both in the liquid phase and in the gas phase.

The invention relates more particularly to a process for separating para-xylene or meta-xylene at high purity (i.e. a purity greater than or equal to 90%) in a simulated moving bed starting from a feed of aromatic hydrocarbons containing isomers with 8 carbon atoms comprising the following steps:

a) a step of bringing the feed in contact, in suitable conditions of adsorption, with a bed containing the selected adsorbent, so as to adsorb para-xylene or meta-xylene preferentially, b) a step of bringing the bed of adsorbent in contact, in conditions of desorption, with a desorbent, the desorbent preferably being either toluene, or para-diethylbenzene, c) a step of withdrawing, from the bed of adsorbent, a stream containing the desorbent and the feed products the least selectively adsorbed, d) a step of withdrawing, from the bed of adsorbent, a stream containing the desorbent and the required product, namely para-xylene or meta-xylene, e) separating the stream resulting from step c) into a first stream containing the desorbent and a second stream containing the feed products the least selectively adsorbed, f) separating the stream resulting from step d) into a first stream containing the desorbent and a second stream containing para-xylene or meta-xylene at a level of purity greater than or equal to 90%, preferably greater than or equal to 99%, and very preferably greater than or equal to 99.7%.

The process for separating para-xylene or meta-xylene can also optionally include the following steps:

g) a step of crystallization in a crystallizer consisting of crystallization of the para-xylene resulting from step f), giving on the one hand crystals of para-xylene impregnated with their mother liquor, and on the other hand a mother liquor that can be partly, or even completely, recycled mixed with the fresh feed at the inlet of the simulated moving-bed adsorption unit, h) a step of washing the crystals resulting from step g), at the end of which para-xylene or meta-xylene is recovered at a purity of at least 99.7%, and preferably of at least 99.8%.

More precisely, the aim of the invention is to optimize the adsorbent solid employed in the process for separating para-xylene or meta-xylene by simulated moving-bed adsorption, to maximize the performance of this process. In general, the performance required for separating a feed containing xylenes is maximum productivity for a purity of the required product in the stream of extract at least equal to 99.5% and even 99.9%, and an overall yield of the required product at least equal to 90%, or even greater than 95% and preferably greater than 97%.

In the present invention, the adsorbent solid used is a zeolitic adsorbent based on zeolite crystals, preferably of zeolite X, LSX or Y, and optionally of non-zeolitic phase (i.e. residual binder, amorphous phase, crystalline phases such as quartz etc. after zeolitization etc.), and in said adsorbent the crystals have a number-average diameter less than or equal to 1.2 μm, preferably between 0.1 μm and 1.2 μm, and preferably between 0.5 μm and 0.8 μm.

When the agglomerate according to the present invention is prepared starting from zeolite X or LSX, the Si/Al atomic ratio is between 1 and 1.5, preferably between 1.2 and 1.3, and the agglomerate comprises:

i. a content of barium oxide BaO and a content of potassium oxide $K_2O$ such that the ratio of the number of moles of the total barium oxide+potassium oxide ($BaO+K_2O$) to the number of moles of the total ($BaO+K_2O+Na_2O$) is greater than 90%.

ii. a content of potassium oxide $K_2O$ such that the ratio of the number of moles of potassium oxide $K_2O$ to the number of moles of barium oxide BaO is less than 50%.

iii. and a total content of oxides of alkali-metal or alkaline-earth ions other than barium and potassium preferably less than 5% and preferably ranging from 0 to 2 wt % and advantageously ranging from 0 to 1 wt % relative to the total weight of the anhydrous zeolitic adsorbent.

When the zeolitic adsorbent according to the present invention is prepared starting from zeolite Y, the Si/Al atomic ratio is between 1.5 and 6, preferably between 2.5 and 3, and the zeolitic adsorbent comprises i. A content of sodium oxide $Na_2O$ and a content of lithium oxide $Li_2O$ such that the ratio of the number of moles of sodium oxide $Na_2O$ to the number of moles of the total sodium oxide+lithium oxide ($Na_2O+Li_2O$) is greater than 65%.

ii. and a total content of oxides of alkali-metal or alkaline-earth ions other than sodium and lithium preferably less than 5% and preferably ranging from 0 to 2 wt % and advantageously ranging from 0 to 1 wt % relative to the total weight of the anhydrous zeolitic adsorbent.

The zeolitic adsorbents according to the invention have a (number-) average particle diameter between 150 μm and 500 μm, preferably between 200 μm and 400 μm and preferably with a granulometric distribution such that there is no particle with size less than 100 μm.

When the zeolitic adsorbents according to the present invention are prepared starting from zeolite X or LSX, they preferably have a grain density between 1.1 and 1.4 g/mL, and preferably between 1.1 and 1.3 g/mL as measured by mercury intrusion (expressed relative to the dry mass of the zeolitic adsorbent) and a pore volume measured by mercury intrusion (pore volume contained in the macropores and the mesopores with apparent diameter greater than 4 nm) between 0.20 and 0.35 mL/g (expressed relative to the dry mass of the zeolitic adsorbent).

The zeolitic adsorbents used in the present invention are obtained conventionally by a process comprising the following steps:

1/ mixing the crystals of zeolite X, LSX or Y as powder of the desired granulometry, in the presence of water with at least one binder based on a clay or a mixture of clays, 2/ forming the mixture obtained in 1/ to produce agglomerates, optionally followed by a step of sieving and/or of cycloning, 3/ calcination of the agglomerates obtained in 2/ at a temperature in the range from 500° C. to 600° C., 4/ (optionally) zeolitization of the binder by contacting the product resulting from 3/ with a basic alkaline aqueous solution followed by washing;

5/ ion exchange of the zeolitic agglomerates based on zeolite X or LSX obtained in 3/ or in 4/ with barium ions alone or with barium ions and potassium ions and optionally partial ion exchange of the zeolitic agglomerates based on sodium zeolite Y obtained in 3/ or in 4/with lithium ions, followed by washing and drying of the product thus treated;

6/ activation of the product resulting from step 5 at a temperature in the range from 200 to 300° C.

Step 2/ of forming can give zeolitic agglomerates having sufficient mechanical strength for use in a process for separating xylenes in a simulated moving bed. However, the presence of binder reduces the proportion of material that is active in the sense of adsorption (zeolite X, LSX or Y).

The optional step 4/ of zeolitization of the binder thus allows some or all of the binder to be converted into material that is active in the sense of adsorption (zeolite X, LSX or Y) in order to obtain "binderless" agglomerates, i.e. no longer comprising non-zeolitic phase or in an amount typically less than 1% or "binderlow" agglomerates, i.e. comprising little non-zeolitic phase, i.e. generally from the non-zeolitized residual binder or any other amorphous phase after zeolitization, in an amount typically between around 2 and 5% in the final agglomerate, while maintaining the mechanical strength. The proportion of non-zeolitic phase (i.e. non-zeolitized residual binder, amorphous phase, after zeolitization) in the final agglomerate can be quantified by reference to an adsorbent composed solely of zeolite, in the form of powder, on the basis of measurements of adsorption or on the basis of intensities of XRD peaks. The reference zeolite is the zeolite used in step 1/ of the process for producing the adsorbent, and that has undergone the same ion exchange.

The crystals of zeolites X, LSX or Y resulting from zeolitization of the binder (conversion of the binder to zeolite) are generally of smaller diameters than the initial crystals. Consequently, in the final agglomerate, the crystals whose average diameter is less than or equal to 1.2 µm, preferably between 0.1 µm and 1.2 µm, and preferably between 0.5 µm and 0.8 µm, conventionally display a monomodal granulometric distribution, but we remain within the scope of the invention if the distribution of the diameters of the crystals is multimodal, and in particular bimodal, owing to the presence of the population of crystals resulting from zeolitization of the binder.

The performance of the zeolitic adsorbents, as described above, for the process for separating para-xylene or meta-xylene, in terms of purity of para-xylene or of meta-xylene in the extract and yield of the process, is influenced by various parameters of the process, namely the operating conditions, the composition of the initial feed, the water content and the type of desorbent.

The operating conditions of the industrial unit for simulated counter-current adsorption using the zeolitic adsorbents as described above are typically as follows:
  number of beds between 4 and 24
  number of zones: at least 4
  temperature 100° C. to 250° C., preferably 150° C. to 190° C.,
  pressure between the bubble pressure of the xylenes at the process temperature and 3 MPa
  cycle time, corresponding to the time between two injections of desorbent on a given bed, between 4 and 18 min
  ratio of the flow rates of desorbent to feed 0.7 to 2.5
  recycling rate (ratio of the average flow rate of the zones weighted with the number of beds present in each zone to the feed flow rate) from 2 to 12, preferably 2.5 to 4.

The desorbent is preferably either toluene or para-diethylbenzene when the compound to be separated is para-xylene and preferably either toluene or indane when the compound to be separated is meta-xylene.

The water content of the hydrocarbon effluents is preferably adjusted between 20 ppm and 150 ppm for the adsorbents based on zeolite X and LSX for a process temperature from 165° C. to 185° C., in order to obtain results that are optimum for productivity.

The water content of the hydrocarbon effluents is preferably adjusted between 0 and 80 ppm for the adsorbents based on zeolite Y for a process temperature from 120° C. to 180° C., in order to obtain results that are optimum for productivity.

Techniques for Characterization of the Zeolitic Adsorbents

For estimating the number-average diameter of the adsorbent solids obtained at the end of step 2/ of forming, it is necessary to carry out an analysis of the granulometric distribution of a sample of adsorbent by imaging according to standard ISO 13322-2: 2006 using a conveyor belt to enable the sample to pass in front of the camera lens.

The number-average diameter is then calculated from the granulometric distribution, applying standard ISO 9276-2: 2001. In the present document, the designation "number-average diameter" or else "size" is used for the particles of zeolitic adsorbents. The precision is of the order of 10 µm for the size range of zeolitic adsorbents of the invention.

The number-average diameter of the crystals of zeolite X, LSX or Y contained in the zeolitic adsorbents is estimated by observation with the scanning electron microscope (SEM). In order to estimate the size of the zeolite crystals from the samples, a set of images is obtained at a magnification of at least 5000. The diameter of at least 200 crystals is then measured using dedicated software, for example the Smile View software (publisher: LoGraMi). The number-average diameter is then calculated from the granulometric distribution, applying standard ISO 9276-2: 2001.

The designation "number-average diameter" or else "size" is employed for the zeolite crystals. The precision is of the order of 3%.

SEM observation of the zeolitic adsorbents also makes it possible to confirm the presence of non-zeolitic phase comprising for example residual binder (not converted during the zeolitization step) or any other amorphous phase in the agglomerates.

Elemental chemical analysis of the adsorbent can be carried out by various analytical techniques known by a person skilled in the art. Among these techniques, we may mention the technique of chemical analysis by X-ray fluorescence as described in standard NF EN ISO 12677: 2011 on a wavelength dispersive spectrometer (WDXRF), for example Tiger S8 from the company BRUKER.

X-ray fluorescence is a spectral technique that offers precise determination, both quantitative and qualitative, except for the lightest elements such as lithium, sodium or potassium present at very low contents. In this case, inductively coupled plasma atomic emission spectrometry (ICP-AES) will be preferred, described in standard NF EN ISO 21079-3, for example on apparatus of the Perkin Elmer 4300DV type.

These elemental chemical analyzes make it possible both to verify the Si/Al atomic ratio of the zeolitic adsorbent, and measure the contents of oxides of alkali-metal or alkaline-earth ions and notably BaO, $K_2O$, $Na_2O$, $Li_2O$.

It should be noted that the contents of different oxides are given, regardless of the technique, as percentage by weight relative to the total weight of the anhydrous adsorbent.

The mercury intrusion technique is used for characterizing the intragranular pore volume contained in the pores of the adsorbent with diameters greater than 3.6 nm, and for measuring its grain density. A mercury porosimeter of the Autopore 9500 Micromeritics type is used for analysing the distribution of the pore volume contained in the macropores with pore diameter >50 nm and in the mesopores between 3.6 and 50 nm. The micropore volume within the zeolite crystals as well as the pore volume contained in the small mesopores between 2 and 3.6 nm are not accessible with the existing porosimeters. The experimental method described in the operating manual of the apparatus consists of putting a previously weighed sample of adsorbent (of known loss on ignition) in a cell of the porosimeter, then, after first degassing (evacuation pressure of 30 µm Hg for at least 10 min), filling the cell with mercury at a given pressure (0.0036 MPa), and then applying a pressure increasing in stages to 400 MPa for gradual penetration of the mercury into the porous network of the sample. The relation between the pressure applied and the diameter of the pores is established on the assumption of cylindrical pores, a contact angle between the mercury and the wall of the pores of 140° and a surface tension of the mercury of 485 dynes/cm.

The cumulative amount of mercury introduced is recorded as a function of the pressure applied. The apparatus cannot differentiate between intergranular volume and intragranular volume: it is assumed that at about 0.2 MPa (corresponding to apparent pore diameters of 7 μm), the mercury fills all the intergranular voids, and in addition the mercury penetrates into the pores of the adsorbent. The grain density of the adsorbent is thus calculated by dividing the sample mass by the sample volume evaluated from the volume of mercury introduced at a pressure of 0.2 MPa.

The total pore volume of the adsorbent is then evaluated from the total volume of mercury introduced, corrected with the volume of mercury introduced at a pressure of 0.2 MPa.

In the present document, the grain density and the pore volume of the zeolitic adsorbents measured by mercury intrusion are referred to the mass of the anhydrous sample (by correcting the loss on ignition of the sample analyzed).

The technique for characterization of the mechanical strength representative of crushing of the adsorbent within a bed or a reactor is the technique for characterization of the mechanical strength in a bed, as described in the Shell method series SMS1471-74 (Shell Method Series SMS1471-74 Determination of Bulk Crushing Strength of Catalysts. Compression-Sieve Method), combined with the "BCS Tester" apparatus marketed by the company Vinci Technologies. This method, originally intended for characterization of catalysts from 3 to 6 mm, is based on the use of a 425 μm sieve, which will notably make it possible to separate the fines created during crushing. The use of a 425 μm sieve is still suitable for particles with a diameter greater than 1.6 mm, but must be adapted according to the granulometry of the zeolitic adsorbents that are to be characterized. Standard ASTM D7084-04, which also describes a method for measuring the crushing strength in a catalyst bed ("Determination of Bulk Crush Strength of Catalysts and Catalyst Carriers") defines the passage of the sieve to be used as being equal to half the diameter of the catalyst particles to be characterized. The method specifies a preliminary step of sieving the sample of catalysts or adsorbents to be characterized. If an amount equal to 10 wt % of the sample passes through the grid, a sieve with smaller passage will be used.

The zeolitic adsorbents of the present invention are in the form of beads or extrudates, and have a number-average diameter ranging from 150 μm to 500 μm, and preferably ranging from 200 μm to 400 μm. Preferably, no particle has a size smaller than 100 μm. Consequently, a 100 μm sieve will be used in place of the 425 μm sieve mentioned in the Shell standard SMS1471-74 method.

The method takes place as follows: a 20 cm³ sample of agglomerated adsorbents, sieved beforehand with the appropriate sieve (100 μm) and previously dried in a stove for at least 2 hours at 250° C. (instead of 300° C. mentioned in the Shell standard SMS1471-74 method), is placed in a metal cylinder of known internal section. An increasing force is imposed in stages on this sample by means of a piston, through a 5 cm³ bed of steel beads for better distribution of the force exerted by the piston on the agglomerates of adsorbents (use of beads of 4 mm diameter for analysis of all the types of extrudates and the particles of spherical shape having a diameter >1.6 mm, and beads of 2 mm diameter for particles of spherical shape with diameter <1.6 mm). The fines obtained at the different pressure stages are separated by sieving (suitable 100 μm sieve) and weighed. The bed crushing strength is determined by the pressure in megapascal (MPa) for which the amount of cumulative fines passing through the sieve rises to 0.5 wt % of the sample. This value is found by plotting a graph of the mass of fines obtained as a function of the force applied on the bed of adsorbent and by interpolating to 0.5 wt % of cumulative fines. The bed crushing strength is typically between some hundreds of kPa and some tens of MPa and is generally between 0.3 and 3.2 MPa.

The precision is conventionally below 0.1 MPa.

EXAMPLES

Example 1: Reference Formulation Ref. (Comparative)

In this example, a zeolitic adsorbent based on BaX forming 1.5 μm crystals, formed as beads with diameter of 0.6 mm, is used for simulated moving-bed separation of para-xylene. The adsorbent is prepared by the method of manufacture described in patent application WO08/009845.

A unit with simulated moving-bed operation is used, consisting of 24 beds, with a length of 1.1 m, with injection of feed, injection of desorbent, withdrawal of extract and withdrawal of raffinate. The beds are distributed in 4 chromatographic zones according to the configuration: 5/9/7/3.

The feed is composed of 21.6% of para-xylene, 20.8% of ortho-xylene, 47.9% of meta-xylene and 9.7% of ethylbenzene. The desorbent is para-diethylbenzene. The temperature is 175° C., and the pressure is 15 bar. The water content is 95 ppm (by weight).

The reference productivity is 70 kg of para-xylene/m³/h. The linear surface velocity in zone 3 is 1.63 cm/s.

Example 2: Formulations A to D (According to the Invention)

The performance of the different formulations according to the invention in a simulated moving bed is evaluated and expressed as gain in productivity relative to the preceding reference example. The objective of maximum linear surface velocity in zone 3 is maintained at 1.65 cm/s.
Formulation A: 300 μm beads consisting of 1.2 μm crystals
Formulation B: 300 μm beads consisting of 0.3 μm crystals
Formulation C: 200 μm beads consisting of 0.8 μm crystals
Formulation D: 200 μm beads consisting of 0.5 μm crystals Moreover, mock-up tests reproducing a section of an adsorber (upper distributing element, bed of adsorbent and lower distributing element) were conducted with formulations A to D in order to observe possible formation of furrows or banks on the surface of the granular bed, which is detrimental for the productivity in the long term.

For all the formulations A to D, no formation of furrows or banks on the surface of the granular bed is observed at the maximum linear surface velocity of 1.65 cm/s (FIG. 2), i.e on the photographs, no deformation of the surface of the granular bed is observed relative to the horizontal line passing by the initial bed surface at the beginning of the test.

Example 3: Formulations E and F (Comparative)

Formulations with smaller granulometry than that of examples A to D are tested and the gain in productivity relative to the comparative example is evaluated. The objective of maximum linear surface velocity in zone 3 is maintained at 1.65 cm/s.

Formulation E: 100 μm beads consisting of crystals of 1.2 μm

Formulation F: 100 μm beads consisting of crystals of 0.5 μm

Mock-up tests were also carried out with formulations E and F, and show formation of furrows or banks on the surface of the granular bed for linear surface velocities below 1.65 cm/s (FIG. 3). After 4 hours under flow, a deformation of the bed surface is observed in such a way that the lowest and/or the highest point of the height profile of the bed is at least 10% different from the initial height of the granular bed.

Example 4: Results

Table 1 presents the results of the mock-up test on the different formulations A, B, C, D, E, F relative to the reference Ref.

It appears that choosing a granulometry according to the invention for the particles of adsorbent solid, combined with small size of zeolite crystals, can give good initial productivity, while avoiding the formation of banks, which allows this productivity to be maintained in the long term.

|  | Diameter of the beads (μm) | Diameter of the crystals (μm) | Mechanical crushing strength (MPa) | Velocity in zone 3 (cm/s) | Gain in initial productivity/ Ref. | Formation of banks |
|---|---|---|---|---|---|---|
| Ref. (comparative) | 600 | 1.5 | 2.4 | 1.63 |  | No |
| A | 300 | 1.2 | 2.5 | 1.28 | 2.4 | No |
| B | 300 | 0.3 | 2.0 | 1.60 | 6.7 | No |
| C | 200 | 0.8 | 2.3 | 1.63 | 5.9 | No |
| D | 200 | 0.5 | 2.1 | 1.66 | 9.0 | No |
| E (comparative) | 100 | 1.2 | — | 1.50 | 3.7 | Yes |
| F (comparative) | 100 | 0.5 | — | 1.65 | 9.2 | Yes |

The invention claimed is:

1. A process for separating xylenes starting from a feed comprising cuts of isomers of aromatic hydrocarbons containing 8 carbon atoms, the process comprising selectively adsorbing a xylene isomer from the feed in a simulated moving bed in the presence of a desorbent, using particles of agglomerated zeolitic adsorbent based on zeolite crystals with a number-average diameter less than or equal to 1.2 μm, wherein the number-average diameter of said particles of adsorbent is between 150 μm and 500 μm, limits excluded, and the mechanical strength measured by the Shell method series SMS1471-74 adapted for agglomerates with a size below 500 μm is greater than or equal to 2 MPa.

2. The process for separating xylenes according to claim 1, wherein the number-average diameter of said particles of agglomerated zeolitic adsorbent is from 200 μm to 400 μm, limits included.

3. The process for separating xylenes according to claim 1, wherein the granulometric distribution of said particles of adsorbent is such that there is no particle with size less than 100 μm.

4. The process for separating xylenes according to claim 1, wherein the number-average diameter of the zeolite crystals is between 0.1 μm and 1.2 μm.

5. The process for separating xylenes according to claim 4, wherein the number-average diameter of the zeolite crystals is between 0.5 μm and 0.8 μm.

6. The process for separating xylenes according to claim 1, wherein the process is carried out in a simulated moving-bed unit having the following characteristics:
   number of beds between 4 and 24
   number of zones: at least 4, wherein each zone has a zone flow rate.

7. The process for separating xylenes according to claim 6, wherein the cycle time, corresponding to the time between two injections of desorbent on a given bed, is between 4 and 18 min.

8. The process for separating xylenes according to claim 1, wherein the adsorption is carried out at a temperature from 100° C. to 250° C., and at a pressure between the bubble pressure of the xylenes at the process temperature and 3 MPa.

9. The process for separating xylenes according to claim 6, wherein the ratio of the flow rates of desorbent to feed is between 0.7 and 2.5 and a recycling rate, representing a ratio of the average flow rate of the zones weighted with the number of beds present in each zone to a feed flow rate, is between 2.0 and 12.

10. The process for separating xylenes according to claim 1 wherein the xylene which is selectively adsorbed is para-xylene and wherein the agglomerated zeolitic adsorbent is based on zeolite X or LSX having an Si/Al atomic ratio such that $1.0 \leq Si/Al < 1.5$.

11. The process for separating xylenes according to claim 10, wherein the agglomerated zeolitic adsorbent further comprises:
   i. a content of barium oxide BaO and a content of potassium oxide $K_2O$ such that the ratio of the number of moles of the total barium oxide+potassium oxide $(BaO+K_2O)$ to the number of moles of the total $(BaO+K_2O+Na_2O)$ is greater than 90%;
   ii. a content of potassium oxide $K_2O$ such that the ratio of the number of moles of potassium oxide $K_2O$ to the number of moles of barium oxide BaO is less than 0.5; and
   iii. a total content of oxides of alkali-metal or alkaline-earth ions other than barium and potassium is below 5% relative to the total weight of the agglomerated zeolitic adsorbent.

12. The process for separating xylenes according to claim 10, wherein the agglomerated zeolitic adsorbent has a grain density between 1.1 and 1.4 g/mL, as measured by mercury intrusion (expressed relative to the dry mass of the zeolitic adsorbent) and a total pore volume measured by mercury intrusion (pore volume contained in the macropores and the mesopores with apparent diameter greater than 4 nm) between 0.20 and 0.35 mL/g (expressed relative to the dry mass of the zeolitic adsorbent).

13. The process for separating xylenes according to claim 10, wherein the process carried out at a temperature from 165° C. to 185° C. and wherein the water content of the hydrocarbon effluents is adjusted between 20 ppm and 150 ppm, by adding water to the feed comprising the cuts of isomers of aromatic hydrocarbons containing 8 carbon atoms and/or to the desorbent.

14. The process for separating xylenes according to claim 10, wherein the desorbent is selected from the group consisting of toluene and para-diethylbenzene.

15. The process for separating xylenes according to claim 1, wherein meta-xylene is selectively adsorbed and wherein the agglomerated zeolitic adsorbent is based on zeolite Y having an Si/Al atomic ratio such that 1.5<Si/Al<6.

16. The process for separating xylenes according to claim 15, wherein the agglomerated zeolitic adsorbent further comprises:
   i. a content of sodium oxide $Na_2O$ and a content of lithium oxide $Li_2O$ such that the ratio of the number of moles of sodium oxide to the number of moles of the total sodium oxide+lithium oxide ($Na_2O+Li_2O$) is greater than 65%; and
   ii. a total content of oxides of alkali-metal or alkaline-earth ions other than sodium and lithium below 5% relative to the total weight of the zeolitic adsorbent.

17. The process for separating xylenes according to claim 15, wherein the process is carried out at a temperature from 120° C. to 180° C. and wherein the water content in the hydrocarbon effluents is adjusted between 0 ppm and 80 ppm, by adding water to the feed comprising the cuts of isomers of aromatic hydrocarbons containing 8 carbon atoms and/or to the desorbent.

18. The process for separating xylenes according to claim 15, wherein the desorbent is selected from toluene and indane.

19. The process for separating xylenes according to claim 10, wherein para-xylene is separated in a purity greater than or equal to 90%.

20. The process for separating xylenes according to claim 15, wherein meta-xylene is separated in a purity greater than or equal to 90%.

* * * * *